United States Patent [19]

Powell

[11] Patent Number: 4,803,974
[45] Date of Patent: Feb. 14, 1989

[54] ORAL LAVAGE APPARATUS

[76] Inventor: James R. Powell, 480 Roe Ave., Elmira, N.Y. 14901

[21] Appl. No.: 105,733

[22] Filed: Oct. 7, 1987

[51] Int. Cl.⁴ ............................................. A61H 9/00
[52] U.S. Cl. ...................................... 128/66; 206/368; 222/79
[58] Field of Search ................. 128/62 A, 66; 433/77, 433/80; 15/167.1; 222/79; 206/63.5, 368, 369

[56] References Cited

U.S. PATENT DOCUMENTS

| 1,660,870 | 2/1928 | Fust | 433/31 |
| 1,684,417 | 9/1928 | Silberman | 206/63.5 |
| 2,066,313 | 1/1937 | Barr | 433/31 |
| 2,793,380 | 5/1957 | Brown et al. | 128/62 A |
| 3,144,867 | 8/1964 | Trupp et al. | 128/66 |
| 3,318,482 | 5/1967 | Voce | 222/79 |
| 3,452,745 | 7/1969 | Hutchinson et al. | 128/62 A |
| 3,568,667 | 3/1971 | Krieger | 128/66 |
| 3,674,024 | 7/1972 | Cirillo | 222/79 |
| 3,675,645 | 7/1972 | Samiran et al. | 128/62 A |
| 3,800,786 | 4/1974 | Kovach | 128/62 A |
| 3,930,761 | 1/1976 | Barraclough | 222/79 |
| 4,178,931 | 12/1979 | Lind et al. | 128/66 |
| 4,282,867 | 8/1981 | DuToit | 128/66 |
| 4,512,769 | 4/1985 | Kozam et al. | 433/80 |
| 4,583,531 | 4/1986 | Mattchen | 128/66 |

FOREIGN PATENT DOCUMENTS 2165760  4/1986  United Kingdom ................. 433/77

Primary Examiner—John J. Wilson
Attorney, Agent, or Firm—Fleit, Jacobson, Cohn & Price

[57] ABSTRACT

The present invention relates to an oral lavage apparatus. The apparatus includes a hand-held trigger actuated device for providing liquid in streams of pulses and an external reservoir for holding the liquid to be distributed through the device. The invention is additionally chracterized in that all elements may be easily stored inside the reservoir when the trigger actuated device is not in use. This provides the two-fold benefit of portability while maintaining a sufficient amount of liquid to supply to the hand-held device.

11 Claims, 2 Drawing Sheets

U.S. Patent  Feb. 14, 1989  Sheet 1 of 2  4,803,974
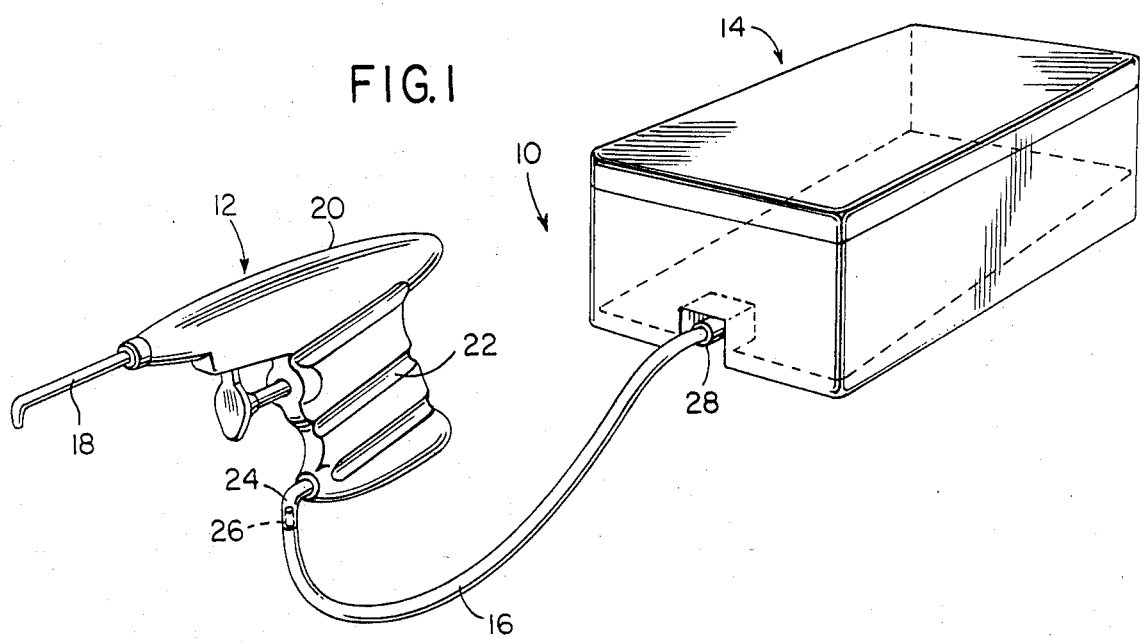
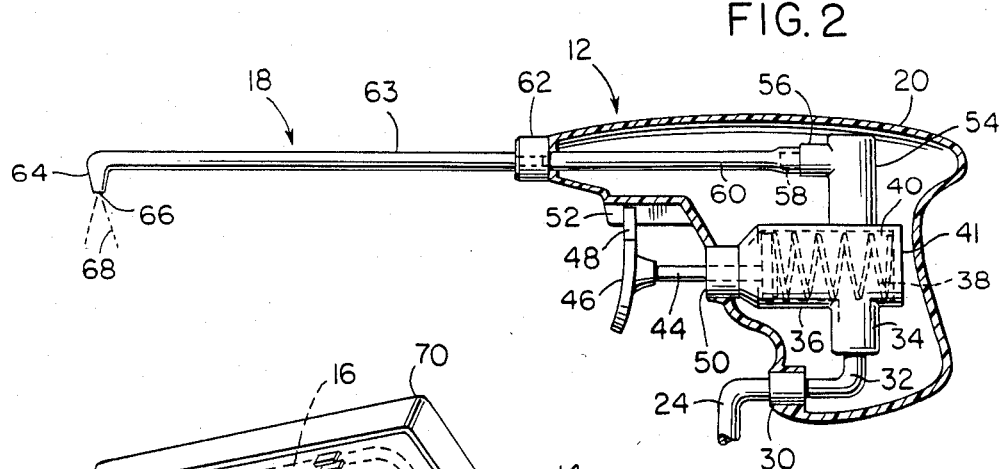
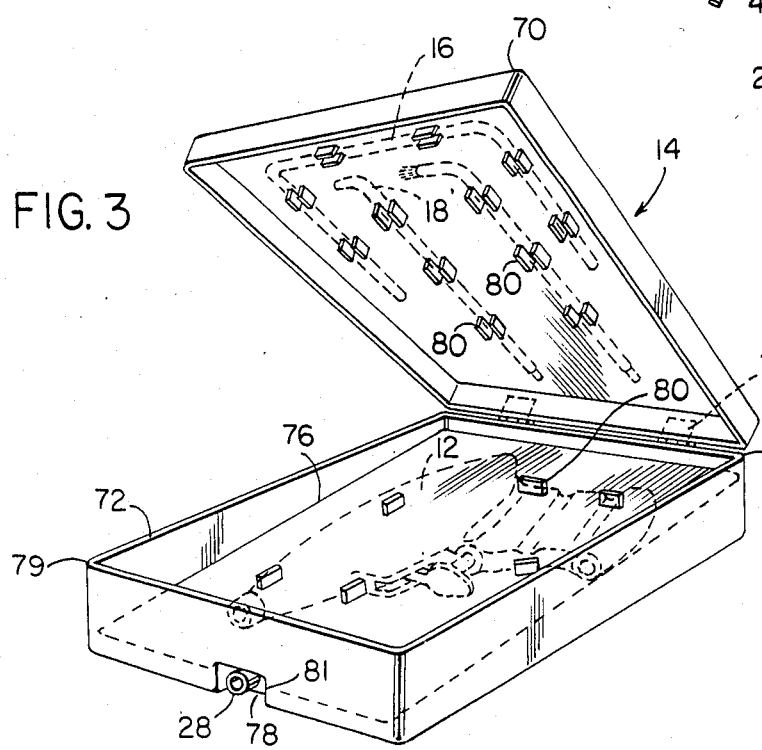
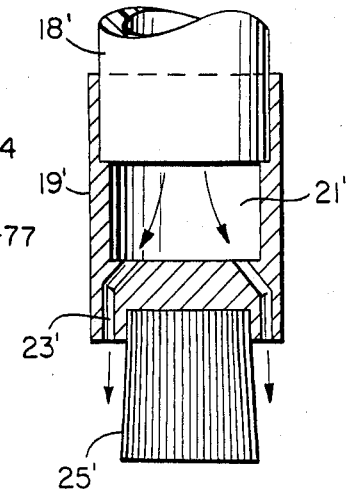

ORAL LAVAGE APPARATUS

BACKGROUND OF THE INVENTION

1. Field of the Invention

The present invention relates to an apparatus for use in oral hygiene, and particularly to an oral lavage apparatus for delivering liquids to the mouth of an individual under controlled conditions for use in the prevention of oral disease during orthodontic care and to aid in the prevention of and in the treatment of periodontal disease.

2. Brief Description of Prior Art

The soft tissues of the mouth are susceptible to pathologies associated with improper oral hygiene in conjunction with infection and the inflammatory processes. Patients in or near these states are in need of regular care of these tissues beyond simple brushing.

Devices have been developed which deliver water and other liquids to the mouth. The devices are designed so that liquid is delivered to the mouth in pressurized streams or pulses. It is particularly advantageous if the streams or pulses can be easily controlled by the patients. For example, many devices presently in commercial use require external means such as electricity to power the device. When using such a device, the patient is limited to work in an area which has electric current located nearby. This may be particularly troublesome if the device is to be used in a school locker room or at an outdoor job site, for example. Accordingly, such electrical devices cannot be considered truly portable.

Although portability is a desirable feature of the user's or patient's device, the device must accommodate enough liquid so that the patient can continuously use it without having to stop to refill the device with the treating liquid.

Although several prior art apparatus have been constructed to meet some of the above described criteria, none have been developed or suggested which can meet all of these criteria.

For example, U.S. Pat. No. 1,660,870 to Fust discloses a mouth mirror which is equipped with a nozzle for ejecting a suitable fluid containing medical substances while boring a tooth. Liquid is delivered to the mirror itself through tubing which is connected to a glass container which holds the liquid. To eject fluid through the mirror, a bulb syringe which is also connected to the reservoir is compressed to force liquid from the reservoir through the tubing into and out of the mirror. The device is deficient in that it is extremely bulky, and the dentist cannot accurately control the streams or pulses due to the bulb actuated syringe.

U.S. Pat. No. 3,452,795 to Hutchinson et al discloses a hand-operated pulsating cleaning device. The device takes the form of a pistol type apparatus, having a pump which is connected to a finger actuated trigger to create the pulses emanating from the device. The reservoir for holding the liquid to be distributed and the discharge nozzle are incorporated into a single structure. Although the Hutchinson et al device is portable, the amount of liquid which may be distributed through the nozzle is limited by the size of the reservoir. Accordingly, to accommodate a sufficient amount of liquid, such as 16 oz., for example, the device would have to be very large and therefore lose its portability feature.

U.S. Pat. No. 3,675,645 to Samiran et al discloses a dental hygiene device. In FIG. 10 of Samiran it is shown that liquid to be used in treating a tooth may be provided in an external reservoir which is connected to a device which discharges the liquid. The device is operated by squeezing a manually operable bulb which is connected to both the device and the reservoir. As is the case with the Fust Patent, the Samiran et al invention is not portable, and the streams of jets of liquid cannot be easily controlled due to the bulb type actuation.

Thus, a need exists for an oral lavage apparatus which can deliver pulses of liquid to a patient's mouth, can be easily actuated by the operator, is portable, and can accommodate an adequate amount of liquid to be distributed.

SUMMARY OF THE INVENTION

The present invention relates to an oral lavage apparatus which is both portable, and can accommodate an adequate amount of liquid. More specifically, the pulses of liquid emanating from the apparatus are produced by utilizing a hand-held pistol type device which is hand actuated by depressing a trigger which is connected to a pump. The pulses, which are ejected through an outlet tube, are controlled by the amount of pressure and number of times the trigger is depressed.

Liquid is provided to the pistol-like device by an external reservoir which holds the liquid, and tubing which connects the reservoir to the device. The system is designed so that when not in use, the pistol-like device, and outlet tube and connecting tubing can be easily stored inside the reservoir after all liquid has been removed from the reservoir.

The device is also particularly designed so that it may be used in addition to ordinary brushing and flossing so that the food and plaque accumulated around braces on teeth, in between teeth, and gums due to periodontal disease can be treated in a simplified way. The portability feature of the present device allows an individual to use the device when at home, or away from home, such as at work, at school, or elsewhere. Further, by using this device, in conjunction with proper treatment, the spread of peridontal disease may be limited and, in some situations, actually reversed.

Thus, it is an object of the present invention to provide an apparatus which can produce a pulsating stream of liquid to the mouth.

It is a further object of the present invention to provide an apparatus which may be easily operated and produces pulsating streams of liquids at a desired frequency.

A further object of the present invention is to provide an oral lavage apparatus which is portable so that it may be used in any number of different locations.

It is an additional object of the present invention to provide an apparatus which is portable, but yet can accommodate a significant amount of liquid to be distributed to the patient's mouth.

It is a further object of the present invention to provide an apparatus wherein all components of the device, not including the liquid reservoir, may be easily stored in the interior of the liquid reservoir when not in use.

It is an additional object of the present invention to provide an apparatus which may use several different types of distribution tips to be used for delivering pulsating streams of liquid to the mouth of the patient.

Other objects and features of the present invention will become apparent to those skilled in the art as the disclosure is made in the following description of the preferred embodiment of the present invention, as illustrated in the accompanying drawings.

BRIEF DESCRIPTION OF THE DRAWINGS

FIG. 1 is a perspective view of the oral lavage apparatus embodying the teachings of the instant invention.

FIG. 2 is a cross sectional view of the pistol-like device of the apparatus of FIG. 1.

FIG. 3 is a perspective view of the interior of the reservoir including retaining means for holding all other elements of the oral lavage apparatus.

FIG. 4 is a view of the tip of an attachment to the pistol-like device wherein the attachment is a brush.

DETAILED DESCRIPTION OF THE DRAWINGS

Figure 5:
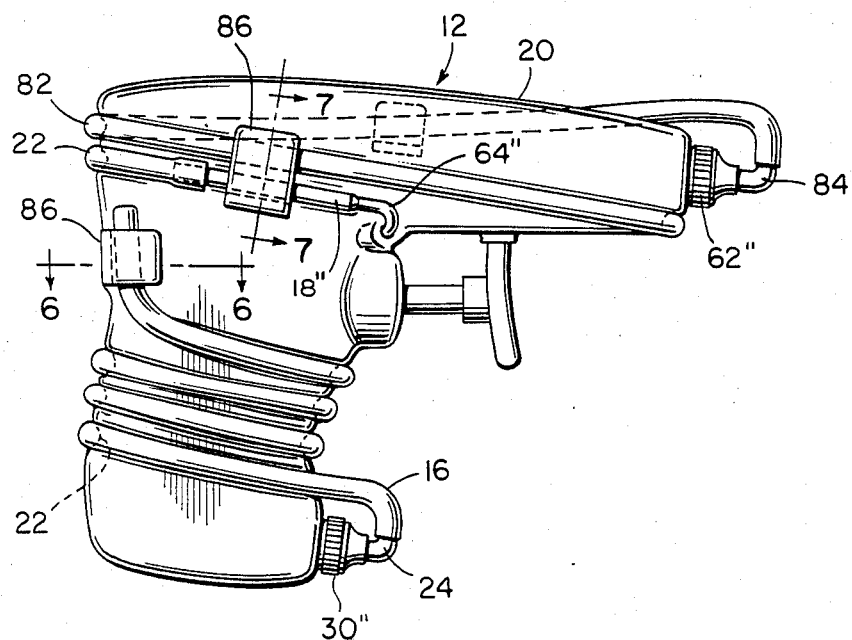
FIG. 5 is a side view of an alternate embodiment of the pistol type device which includes retaining means for holding all connecting and liquid distribution tubes to the exterior surface of the pistol type device.

In describing the invention illustrated in the drawings, specific terminology will be resorted to for the sake of clarity. However, the invention is not intended to be limited to the specific terms so selected, and it is to be understood that each specific term selected includes all technical equivalents which operate in a similar manner to accomplish a similar purpose.

Referring now to the drawings, and more particularly FIG. 1, the basic elements of the oral lavage apparatus are collectively designated as 10. Apparatus 10 includes pistol-like dental jet stream device 12 which is connected to reservoir 14 by connecting tube 16. One end of tube 16 is connected to reservoir 14 at reservoir connection port 28. The other end of tube 16, designated as delivery tube 26 is connected to elbow connecting tube 24, which is connected to device 12.

The external body of device 12, designated as element 20, may contain longitudinal grooves 22. Also attached to device 12 is cleaning jet tube 18 which delivers liquid to the human mouth.

Referring to FIG. 2, the internal portion of device 12 is shown in cross section. Elbow connecting tube 24 is connected to device connecting port 30 at the lower portion of body 20. Inlet fluid tube 32, which takes the shape of an elbow, is connected at one end to device connecting port 30 in the internal portion of device 12. The other end of tube 32 is connected to vertical inlet pipe 34. Although not pictured, vertical inlet pipe 34 also may contain an inlet check valve therein.

Pipe 34 is connected to cylinder 36 along one of the side walls of cylinder 36. Resting inside the interior of cylinder 36 and perpendicular to inlet pipe 34 is coil spring 38. One end of spring 38 rests against end wall 41 of cylinder 36. The other end of spring 38, when in its decompressed state is biased against piston 42. Piston 42 is connected to shaft 44 which passes through outwardly extending journal bearing 50. In this arrangement, one end of shaft 44 is located on the interior of device 12 inside cylinder 36 and the opposite end of shaft 44 is located outside of the interior of device 12.

Connected to the end of shaft 44 outside the interior of device 12 is trigger 46. Located at the top of trigger 46 is upwardly extending lug 48 which is located in channel 52.

Piston 42 and cylinder 36 form a chamber designated by numeral 40. Spring 38 is also located inside chamber 40. The opposite sidewall of cylinder 36 which is not connected to pipe 34 is connected to vertical outlet pipe 54. Although not pictured, vertical outlet pipe 54 may have an outlet check valve contained therein.

Pipe 34, cylinder 36, spring 38, chamber 40, piston 42 and pipe 54 form the pumping mechanism for delivering liquid through device 12. Connected perpendicular to outlet pipe 54 is horizontal connecting pipe 56. Connected at the end opposite the end connected to pipe 54 is connector tube 58 which is connected at its opposite end to outlet tube 60. The end of outlet tube 60 not connected to connector tube 58 may be connected to journal bearing 62 while still in the interior of device 12. Journal bearing 62 abuts the internal portion of device 12 at one end and extends to the exterior of device 12 at its opposite end. At this opposite end, cleaning jet tube 18 is connected to journal bearing 62 so that outlet tube 60 and cleaning jet tube 18 communicate via bearing 62.

Cleaning jet tube 18 consists of shaft 63 which is parallel to outlet tube 60 and shaft 44. The end of shaft 63 is curved approximately 90° and angles downwardly as shown by angled tapering head 64. The portion of head 64 not integral with shaft 63 terminates in opening 66. Opening 66 has a cross sectional area less than the cross sectional area of head 64 when integral with shaft 63. When in use, a stream of liquid 68 exits through opening 66.

Referring to FIG. 3, reservoir 14 is shown in perspective. Reservoir 14 includes rectangular reservoir top 70 which is mounted to rectangular reservoir bottom 72 by mounting means such as hinges 74. The perimeter of top 70 is slightly greater than the perimeter of bottom 72 so that when attached, the lower portion of top 70 overlaps the upper portion of bottom 72.

Reservoir bottom 72 also has angled base 76. Base 76 is angled so that when the portion of bottom 72 is furthest away from reservoir connection port 28 and connecting port chamber 78, the upper portion of base 76 abuts the upper portion of endwall 77 which is connected to top 70. The edge of base 76 which abuts endwall 79 does so towards the lower portion of endwall 79. The portion of base 76 abutting wall 79 must be located below connection port 28.

Connecting port 28 is cylindrically shaped and has a hollow opening through its center or the port 28 may be invaginated. One end of port 28 lies external to bottom 72 while the other end of port 28 directly abuts bottom 72 at wall 81 such that the center opening of port 28 passes through wall 81 and into the interior of bottom 72.

The interior portions of top 70 and base 76 are adapted with retaining means 80 which are used to hold the remaining pieces of the oral lavage apparatus 10 when the pulsating device is not in use. As shown in FIG. 3, apparatus 12 is retained in the interior of base 76 and connecting tube 16, cleaning jet tube 18 and brush jet tube 18' are retained in the interior of top 70.

When device 10 is not in use, reservoir top 70 is lowered onto reservoir bottom 72, and the entire device may be conveniently stored and thereafter transported, if necessary.

To use the oral lavage apparatus according to the instant invention, the following procedure is used. Reservoir top 70 is displaced from reservoir bottom 72 by putting upward pressure on top 70 to pivot hinges 74. All implements stored in the interior of top 70 and base 76 are thereafter removed from their retaining means 80. Connecting tube 16 is then mounted to reservoir 14 at connecting port 28 at one of its ends. The other end of connecting tube 16 is connected to elbow connecting tube 24 which in turn is connected to apparatus connecting port 30. This arrangement therefore allows reservoir 14 to be in fluid communication with apparatus 12. Liquid is thereafter poured into the interior of bottom 72 onto base 76. Because base 76 is angled, by utilizing gravitational forces, the liquid placed into reservoir 14 will always flow towards port 28. After all liquid has been poured into bottom 72, top 70 may be lowered onto bottom 72 to seal the interior of reservoir 14 from the external environment if large amounts of liquid to be supplied are not needed.

Cleaning jet tube 18 is then connected to apparatus 12 by inserting shaft 63 into journal bearing 62 such that shaft 63 is in communication with the interior of apparatus 12 through bearing 62. Once this connection has been made, the lavage device can then be used to deliver jet-like streams of liquid to the patient's mouth.

Before depressing trigger 46, the inlet check valve located in vertical inlet pipe is in an open position to allow liquid to be transported from reservoir 14 through tube 16 into apparatus 12. Correspondingly, the outlet check valve located in vertical outlet pipe 54 is in a closed position. Trigger 46 is then squeezed by a finger and in a horizontal direction as directed by lug 48 through channel 52. This causes shaft 44 and piston 42 to move towards wall 41 and causes piston 42 to compress coil spring 38. This causes a positive pressure wherein liquid passes through vertical inlet pipe 34 into cylinder 38 and through vertical outlet pipe 54.

By depressing trigger 46, inlet check valve of pipe 34 is closed and outlet check valve of pipe 54 is opened. The liquid passes through pipe 54, pipe 56, tube 58, and tube 60 into journal bearing 62 and thereafter through jet tube 18. The liquid is ultimately dispensed through opening 66.

Trigger 46 is thereafter released to cause piston 42 to move towards journal bearing 50 by the action of spring 38. This causes a negative pressure and seals off outlet check valve located in pipe 54 and opens inlet check valve located in pipe 34. Accordingly, liquid travels from reservoir 14 through tube 16 and pipe 34 and into cylinder 36. In short, whenever trigger 46 is depressed, liquid traverses from cylinder 36 into outlet pipe 54 to deliver liquid to tube 18, and when trigger 46 is released, liquid travels from reservoir 14 to cylinder 36 but not into pipe 54.

Since the inward and outward motions of piston 42 alternate with each other, the flow of liquid through outlet pipe 54 will be manifested in the form of pulsations, the frequency of which will be equal to the frequency of oscillations of trigger 46 and piston 42. The force of the pulsating streams flowing through outlet tube 54 will be a function of the speed with which trigger 46 and piston 42 are retracted against the action of spring 38.

Once the lavage device is no longer required to be used, tube 16 is disconnected from port 28 and all remaining liquid in reservoir 14 is discarded. The other end of tube 16 is disconnected from apparatus 12. Cleaning tube 18 is also disconnected from apparatus 12. These components are then placed into the interior portions of reservoir 14 as is defined by retaining means 80.

In the preferred embodiment, device 12 is made of molded, inexpensive hard plastic. However, it is envisioned within the scope of this invention that other materials approved by the United States Food and Drug Administration may be used for this system.

Similarly, in the preferred embodiment, reservoir 14 is made of molded, inexpensive hard plastic. The size of reservoir 14 is preferrably large enough to accommodate an adequate amount of liquid. In the preferred embodiment, the size of the reservoir should be sufficient to accommodate at least 3.5 to 5 ounces of liquid. However, if a larger volume were needed, the reservoir could be designed to accommodate at least 16 ounces of liquid. In any event, the reservoir is designed so that the lavage device can be used continuously without interruption. Additionally, the reservoir may be placed in a sink to enable a voluminuous supply of liquid to be provided to the lavage device.

In the preferred embodiment of the invention, retaining means 80 may either be brackets, clamps or hangers.

In the preferred embodiment of the invention, all tubing is made of rubber. However, other types of tubing, such as teflon type may be utilized within the scope of this invention.

In the preferred embodiment of the invention, top 70 is connected to bottom 72 by hinges 74. However, it is contemplated within the scope of this invention that other connecting means such as a snap on lid may be used in lieu of hinges.

Although FIGS. 1 and 2 show the apparatus having a cleaning jet tube 18 connected to apparatus 12, other tips may be used with apparatus 12.

Figure 8:
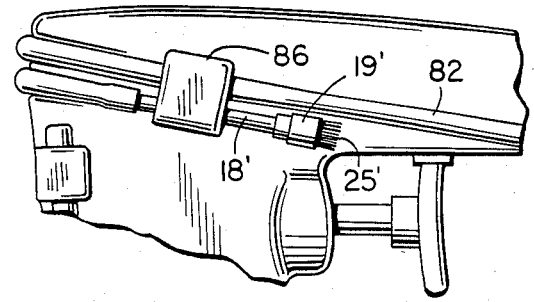
FIG. 8 is a cutaway view of the device embodied in FIG. 5 wherein the attached element is a brush.

For example, FIGS. 4 and 8 show a brush jet tube designated by numeral 18'. As seen in cross section in FIG. 4, tube 18' is connected to brush connecting tube 19' to form chamber 21'. Drilled through the portion of tube 19' which is not connected to tube 18' are fluid ports 23'. Integrally connected, at the tip of connecting tube 19' is brush 25' which may be used to brush the teeth while working with the lavage device. In operation, when trigger 46 is depressed, pulsatng streams of liquid flow through tube 18' into chamber 21' and through fluid ports 23'.

In an alternate embodiment, another longitudinal cylindrical fluid port, not pictured, may be formed through the center of tube 19' and through the center of brush 25' for delivering liquid through brush 25'.

Another alternative cleaning tip is shown in FIG. 5 and is designated by 18". This tip is characterized by having hooked head 64". The curvature of head 64" is such that it exceeds 90°.

Figure 7:
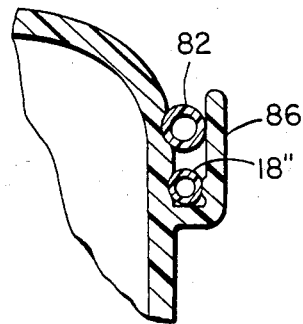
FIG. 7 is a view taken along line 7—7 of FIG. 5.
Figure 6:
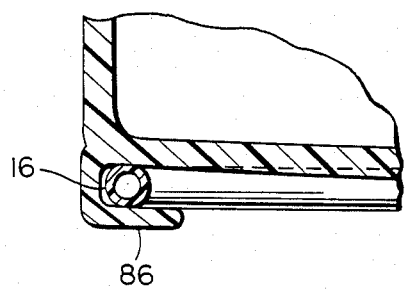
FIG. 6 is a view taken along line 6—6 of FIG. 5.

In an additional embodiment of the lavage device according to the instant invention, the pistol-like dental jet stream device 12 may be provided with retaining means 86 on its exterior surface to hold all connecting tubing. Referring to FIG. 5, retaining means 86 take the form of clips which are molded integrally with the plastic and are designed to hold tubing 16, 82 and 18". Tubing 16 and 82 are designed to rest in grooves 22 as shown in phantom in FIG. 5. The diameter of tubing 16 and 82 is designed so that it approximates the diameter of grooves 22. If this arrangement is used, no retaining means on the interior of reservoir 14 are necessary for holding the tubing. Rather, as shown in FIGS. 6 and 7 in cross section, the tubing is directly pressed between retaining means 86 and body 20.

Although in this embodiment clip 86 is designed to be molded integrally with body 20, the clips may be externally attached to body 20 by means such as glue or fasteners. Further clip 86, although preferrably made of integrally molded plastic, may be made of any suitable material, such as metal or the like.

To enable the user to locate the jet tubes or brush tubes in hard to reach areas, the jet tube or brush tube may be connected to extension tubing to increase the effective length of the jet tube or brush tube. Such an assembly is shown in FIG. 5. Flexible tube 82 is connected to elbow tube 84 which in turn is connected to swivel apparatus connecting port 62". The opposite end of flexible tube 82 is connected to cleaning tip 18". Accordingly, the effective length of cleaning tip 18" is equal to the length of tube 82 and the length of tube 18" less the amount of overlap. In this embodiment, it is preferred that tube 82 be made of flexible rubber or plastic.

As further shown in FIG. 5, to enable the user to have maximum freedom of use of apparatus 12, connecting ports 30" and 62" are designed so that they may swivel. Although the connecting ports may be stationary as is shown in FIG. 2 and designated by element numbers 30 and 62, ports 30" and 62" swivel so that the angle of tubing 16 and 82, respectively, may be monitered in any direction within a 360° circle. This is particularly important for connector 62" as this will allow cleaning tip 18" or cleaning brush 18', as shown in FIG. 8, to be manipulated at the desired angle for treatment of the mouth or tooth.

Although not pictured, the various cleaning and brushing tips may include a plastic extension perpendicular to the tube itself. This extension acts as a handle. Additionally, the handle is preferably sized large enough so that the patient cannot swallow the tube if he or she accidentally loses his or her grip on the tube to prevent the tube from being accidentally aspirated or swallowed.

By using the device according to the instant invention, several objectives are met. First, the device is truly portable, not requiring electric power, and can easily be kept in a pocket or purse, especially when the size of the reservoir is approximately 3.5 to 5 ounces. Despite the portability, the use of an external reservoir allows the user to have a liquid supply sufficient enough to prevent the necessity for constant refill. All that is required is a suitable liquid to be placed in the reservoir and a place to expel it.

Additionally, the design of the interior of the reservoir, which enables all components to be stored in the reservoir, provides for true portability and ease of storage.

Further, with the several cleaning and brushing tips which may be used within the scope of the invention, the patient may be able to reach remote areas under and around bridges, splints and braces for the removal of plaque. Moreover, the brush adaptor type device can be used to both brush and deliver liquid to any desired area not necessarily limited to the oral cavity.

From the above, it should be apparent that many modifications and variations of the present invention are possible. It is therefore to be understood that within the scope of the appended claims, the invention may be practiced otherwise than as is specifically described.

What is claimed is:

1. An oral lavage apparatus comprising a hand-held trigger actuated dental jet stream device having pump means therein for delivering liquid through said device into an oral cavity, tube means connected to said device for delivering said liquid to a human mouth, an external reservoir means for containing and supplying liquid to said device, and first connecting means for connecting said external reservoir means to said device, said reservoir means comprising a top portion and a bottom portion, said bottom portion containing second connecting means for connecting said first connecting means to said reservoir means and wherein said top and bottom portions are sized so that when the device is in use said top portion is attached to said bottom portion to enclose the liquid contained in said reservoir means, the interior of said reservoir means comprising retaining means for securing said device, tube means and first connecting means to the interior of said reservoir means when said device is not in use.

2. The apparatus according to claim 1 wherein the reservoir means is sized to accommodate at least 3.5 ounces of liquid.

3. The apparatus according to claim 2 wherein the reservoir means is sized to accommodate 16 ounces of liquid.

4. The apparatus according to claim 1 wherein said device additionally comprises retaining means for securing said tube means and said first connecting means to the exterior of said device when said device is not in use.

5. The apparatus according to claim 4 wherein said retaining means comprises integrally molded clips.

6. The apparatus according to claim 4 wherein said device additionally comprises groove means on the external body of said device for accommodating said tube means and said first connecting means.

7. The apparatus according to claim 1 further comprising hinge means for attaching said top portion to said bottom portion.

8. The apparatus according to claim 1 wherein said top portion snaps onto said bottom portion.

9. The apparatus according to claim 1 wherein said first connecting means comprises flexible rubber tubing.

10. A manually operated liquid discharge apparatus comprising a reservoir containing a supply of liquid, a hand-held pump located remotely from the reservoir, an elongated flexible inlet tube connecting the pump to the reservoir to supply liquid to the pump, a discharge tube connected to the pump for discharging liquid from the pump at a remote discharge point, said pump including a housing having a pistol-type handgrip thereon, a movable trigger mounted on said housing adjacent the handgrip for engagement by the finger of a user holding the handgrip, said trigger being connected to said pump for actuation of the pump in response to movement of the trigger to discharge liquid from the discharge member, said pump housing including groove means partially receiving and storing said inlet and discharge tubes.

11. The structure as defined in claim 10 wherein said reservoir includes a container having an upstanding peripheral wall and an inclined bottom, said inlet tube being connected to the peripheral wall and communicating with the interior of the container at a point slightly above the lowest portion of the inclined bottom, an openable closure on the top of the peripheral wall, support means on the inclined bottom to releaseably retain the pump stored on the inclined bottom, said closure including support means on the lower surface thereof to releaseably support attachments for the discharge tube, said groove means including a spiral groove on the handgrip receiving the inlet tube and a spiral groove on the upper portion of the housing receiving the discharge tube, one end of each tube being connected to the housing, support means releaseably retaining the free end of the inlet tube on the handgrip and support means releaseably retaining the free end of the discharge tube on the upper portion of the housing.

* * * * *